US00PP37129P2

(12) United States Plant Patent
Catt

(10) Patent No.: US PP37,129 P2
(45) Date of Patent: Dec. 9, 2025

(54) ***DEUTZIA* PLANT NAMED 'LISSTODEL'**

(50) Latin Name: ***Deutzia* X *hybrida***
Varietal Denomination: LISSTODEL

(71) Applicant: Vincent Catt, Hampshire (GB)

(72) Inventor: Vincent Catt, Hampshire (GB)

( * ) Notice: Subject to any disclaimer, the term of this patent is extended or adjusted under 35 U.S.C. 154(b) by 0 days.

(21) Appl. No.: 19/182,712

(22) Filed: Apr. 18, 2025

(30) Foreign Application Priority Data

Sep. 17, 2024 (QZ) ..... PBR 20242153

(51) Int. Cl.
*A01H 6/48* (2018.01)
*A01H 5/02* (2018.01)

(52) U.S. Cl.
USPC ..... Plt./226

(58) Field of Classification Search
USPC ..... Plt./226
CPC ..... A01H 6/48; A01H 5/02
See application file for complete search history.

*Primary Examiner* — Keith O. Robinson
(74) *Attorney, Agent, or Firm* — Penny J. Aguirre

(57) ABSTRACT

A new cultivar of *Deutzia* plant named 'LISSTODEL' that is characterized by its heavy flower production, its compact plant habit, its flowers that are bi-color; pink with white margins, and its dense branching habit.

3 Drawing Sheets

Genus/species: *Deutzia* X *hybrida*.
Varietal denomination: 'LISSTODEL'.

CROSS REFERENCE TO RELATED APPLICATIONS

This application claims priority to European Community Plant Variety Office (CPVO) Plant Breeder's Rights Application No. 2024/2153 filed Sep. 17, 2024 under 35 U.S.C. 119(f), the entire contents of which is incorporated by reference herein.

BACKGROUND OF THE INVENTION

The present invention relates to a new and distinct *Deutzia* plant of hybrid origin and will be referred to hereafter by its cultivar name, 'LISSTODEL'. 'LISSTODEL' represents a new cultivar of *Deutzia*, a deciduous shrub grown for landscape use.

The new cultivar arose from an ongoing breeding program conducted by the Inventor in Liss Forest, The United Kingdom. The goal of the breeding program was to develop a new cultivar of *Deutzia* with a more compact plant habit and flowers that are more pink in color. The new cultivar arose from a cross made by the Inventor in 2014 between an unpatented and unnamed plant of *Deutzia crenata* as the female parent and various unnamed plants of *Deutzia* as the male parent. The seeds were pooled and the male parent is unknown. The Inventor selected 'LISSTODEL' as a single unique plant amongst the seedlings that resulted from the above crosses in June of 2016.

Asexual propagation of the new cultivar was first accomplished by softwood cuttings in Liss Forest, United Kingdom in 2017 by the Inventor. Asexual propagation by softwood stem cuttings has determined the new cultivar is stable and reproduced true to type in successive generations.

SUMMARY OF THE INVENTION

The following traits have been repeatedly observed and represent the characteristics of the new cultivar and distinguish 'LISSTODEL' as a unique cultivar of *Deutzia*.

1. 'LISSTODEL' exhibits heavy flower production.
2. 'LISSTODEL' exhibits a compact plant habit.
3. 'LISSTODEL' exhibits flowers that are bi-color; pink with white margins.
4. 'LISSTODEL' exhibits a dense branching habit.

The female parent of 'LISSTODEL' differs from 'LISSTODEL' in having a less compact plant habit, less dense branching, and flowers that are whiter in color. 'LISSTODEL' can also be compared to the *Deutzia* cultivars 'Raspberry Sundae' (U.S. Plant Pat. No. 22,685) and 'Pride of Rochester' (not patented). Both 'Raspberry Sundae' and 'Pride of Rochester' are similar to 'LISSTODEL' in having bicolor flowers that are pink with white margins. 'Raspberry Sundae' differs from 'LISSTODEL' in having flowers that are clustered more tightly together on the flowering stem, flowers that are lighter pink in color, and a plant habit that is slightly less upright. 'Pride of Rochester' differs from 'LISSTODEL' in having double flowers that droop and a much taller plant height.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Genesis Plant Marketing, Plantipp, Hayloft, Thompson & Morgan, Telegraph Garden Shop, Dobies, Sutton Seeds, Van Meuwen, Visions Pictures, Coolings Garden Centre, Garten Schlüter, and Leenders Plant B.V.

BRIEF DESCRIPTION OF THE DRAWINGS

The accompanying color photographs illustrate the overall appearance and distinct characteristics of the new *Deutzia*. The photographs were taken of a 4-year-old plant of 'LISSTODEL' as grown in an unheated greenhouse in 23-cm containers in Waddinxveen, The Netherlands.

The photograph in FIG. 1 provides a side view of a plant of 'LISSTODEL' in bloom.

Figure 1:
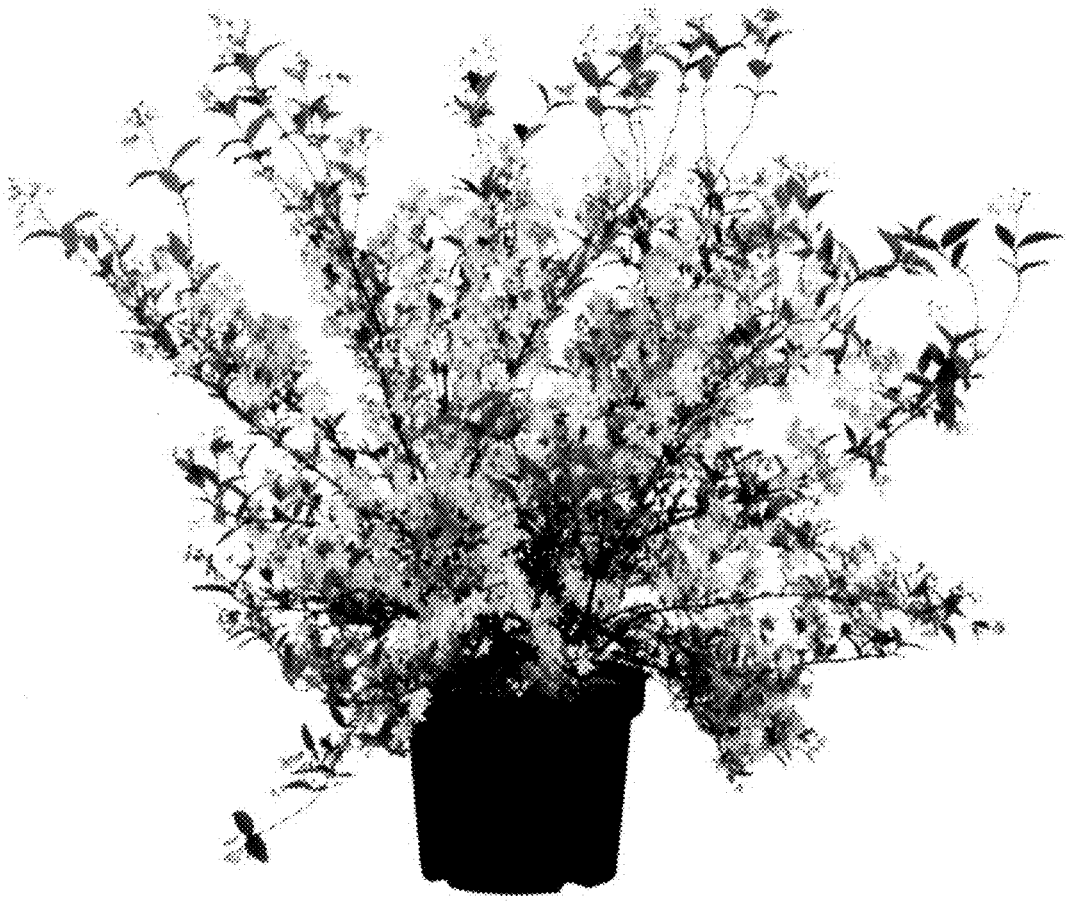
Figure 2:
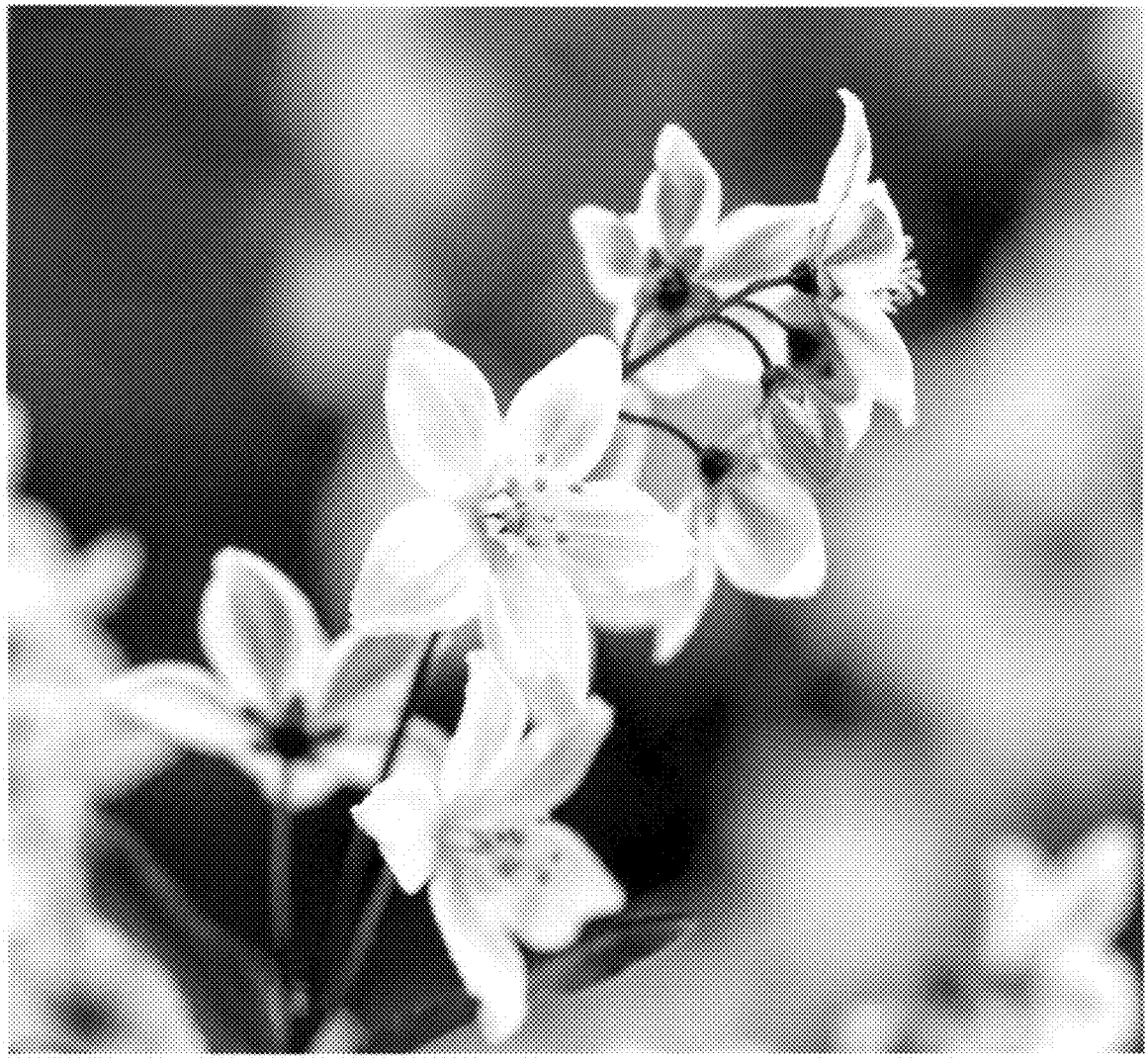

The photograph in FIG. 2 provides a close-up view of the flowers of 'LISSTODEL'.

Figure 3:
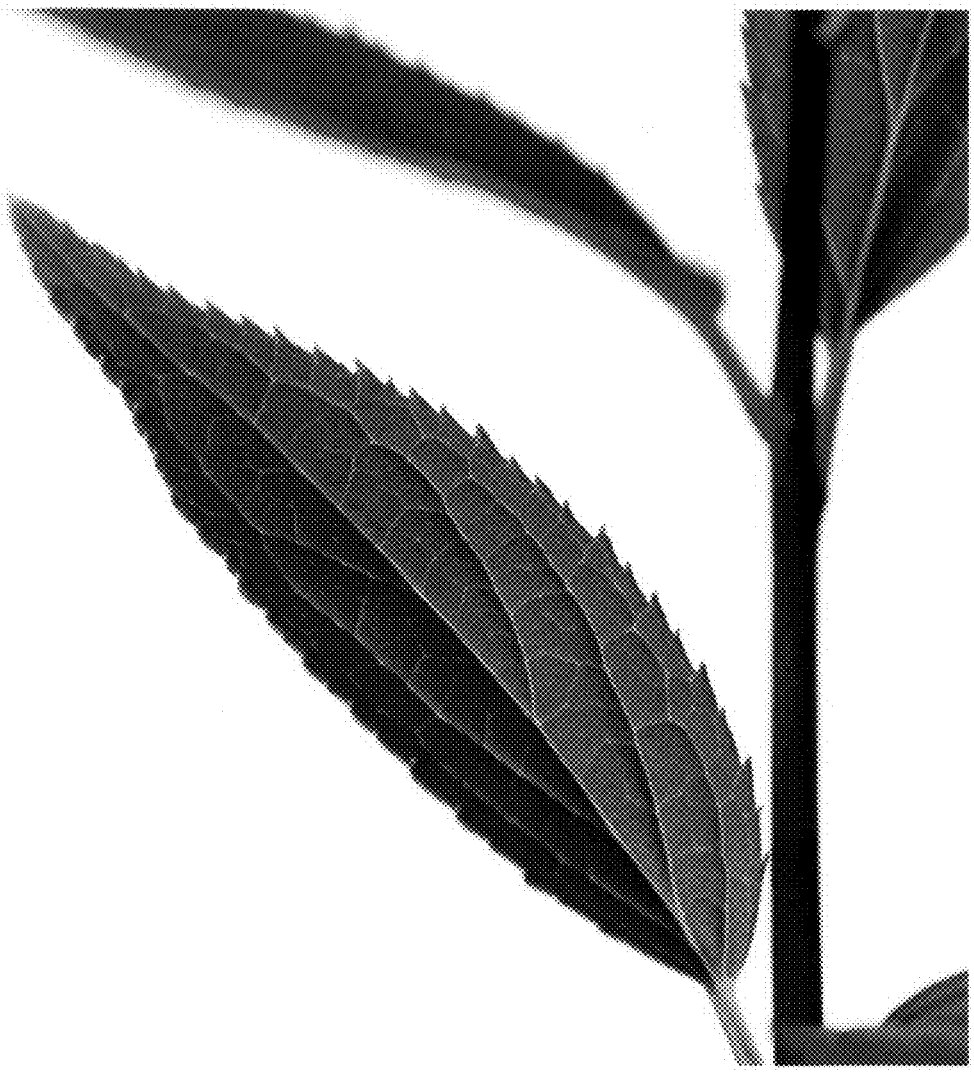

The photograph in FIG. 3 provides a close-up view of a leaf of 'LISSTODEL'.

The colors in the photographs are as close as possible with the photographic and printing technology utilized and the color values cited in the detailed botanical description accurately describe the colors of the new *Deutzia*.

DETAILED BOTANICAL DESCRIPTION

The following is a detailed description of 4-year-old plants of 'LISSTODEL' as grown in an unheated greenhouse in 23-cm containers in Waddinxveen, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—From May through July in the United Kingdom.

*Plant type*.—Deciduous shrub.

*Plant habit*.—Compact, broadly upright to spreading-upright.

*Height and spread*.—An average of 47.5 cm in height from soil level to top of foliar plane, 22 cm in height from soil level to top of floral plane, 38.2 cm in spread as a 4-year-old plant as grown in a container.

*Cold hardiness*.—At least in U.S.D.A. Zone 5a.

*Diseases and pests*.—No susceptibility or resistance to diseases or pests has been observed.

*Root description*.—Fibrous and fine.

*Propagation*.—Softwood stem cuttings.

*Time required for root initiation*.—Root initiation occurs in 3 to 4 weeks, a young plant is produced in 6 to 8 weeks.

*Growth rate*.—Moderate.

Stem description:

*Stem shape*.—Round, solid.

*Stem color*.—Young stems; 148A, tinged N200A, developing stems 183A, mature stems; 148B, slightly tinged and blotched 181B to 181C, internodes; 146D, older stems and bark; 183A and 200A, and a blend of 183A and 200A, shallowly fissured 199C and 199D.

*Stem size*.—Average of 36.5 cm in length, 3 mm in diameter.

*Stem surface*.—Very slightly glossy, glabrous.

*Stem strength*.—Medium.

*Internode length*.—Average of 3 cm.

*Branch quantity*.—Average of 16 main branches, average of 12 secondary branches per main branch.

Foliage description:

*Leaf shape*.—Narrow ovate to near lanceolate.

*Leaf division*.—Simple.

*Leaf base*.—Attenuate.

*Leaf apex*.—Narrow acute, occasionally slightly twisted.

*Leaf venation*.—Pinnate, upper surface color; 144B, lower surface color; 146B.

*Leaf margins*.—Serrate, apices of teeth aristate, undulation none to very low.

*Leaf attachment*.—Petiolate.

*Leaf arrangement*.—Opposite.

*Leaf quantity*.—24 per lateral branch.

*Leaf surface*.—Both surface glabrous and very slightly glossy.

*Leaf size*.—6.4 cm in length, 2.1 cm in width.

*Leaf color*.—Young upper surface; a blend of 143B and 144A, young lower surface; 144A, mature upper surface; 137A, mature lower surface; a blend of 147B and 191A.

*Petiole*.—An average of 6 mm in length and 1.5 mm in diameter, both surfaces smooth and glabrous, upper surface moderately glossy, lower surface matte, color 146C and slightly suffused on lower surface with 183A.

*Stipules*.—None present.

Flower description:

*Inflorescence type*.—Compound cyme.

*Inflorescence size*.—Average of 8.6 cm in height (including peduncle) and 5.5 cm in diameter.

*Natural flowering season*.—Mid-April to mid-May in The Netherlands.

*Flowering habit*.—Freely flowering, self-cleaning.

*Peduncles*.—Average of 5.5 cm in length, 1.2 mm in diameter, held in a vertical angle, moderately strong, smooth and glabrous surfaces, moderately glossy, 146D in color.

*Pedicels*.—Average of 1.8 cm in length, 0.8 mm in diameter, held in a 45° angle, moderately strong, smooth and glabrous surfaces, moderately glossy, 146D in color.

*Bracts*.—None present.

*Flower buds*.—Broadly ovate in shape, smooth glabrous, 8 mm in length, 5 mm in diameter, smooth and glabrous surfaces, matte, color; NN155B to NN155C with a faint central stripe on each immature petal187B, immature sepals 144B and 144C, immature ovary; 138B, with very small glands too small to measure color.

*Flower type*.—Single to semi-double.

*Flower size*.—Average of 1.1 cm in height and 2.8 cm in diameter.

*Flower number*.—Average of 6 per inflorescence, average of 34 per lateral branch.

*Flower lastingness*.—10 days, self-cleaning.

*Flower aspect*.—Held in multiple angles.

*Fragrance*.—No fragrance.

*Calyx*.—Rotate, 2 mm in depth, 7 mm in diameter.

*Sepals*.—Rotate in arrangement, average of 5 in 1 whorl, 3 mm in length, 2 mm in width, un-fused, ovate in shape, acute apex, broadly cuneate base, entire margins, both surfaces smooth, glabrous, matte, color; when opening upper and lower surface 144B, tinged 183D, when fully open upper and lower surface 148D, tinged 183D.

*Petals.*—5, rotate, 1 whorl, 1.35 cm in length, 9 mm in width, obovate to slightly convex in shape, finely praemorse apex, cuneate base, margins entire, finely to irregularly toothed at the top, both surfaces smooth, glabrous, slightly velvety, and matte, color; upper surface when open and fully open, lower surface when opening NN155D, faint central strip 187B, lower surface when fully open NN155D, central stripe 187D.

*Petaloids.*—Average of 4 in 1 whorl, average of 1 cm in length, 6 mm in width, finely praemorse apex, cuneate base, margins entire, finely irregularly toothed at the apex, both surfaces smooth, glabrous, slightly velvety, and matte, upper and lower surface when open and fully open, NN155D, central stripe 187B.

Reproductive organs:

*Androecium.*—Stamens; 10, anther; basifixed, circular, 1 mm in length and width, 7A in color, filaments; winged, an average of 5 mm in length, 0.4 mm in width, pollen; low to moderate 11A to 11B in color.

*Gynoecium.*—Pistils; 3, 7 mm in length, stigma; club-shaped, 1 mm in length, 0.5 mm in diameter, 157D in color, style; average of 6 mm in length, color 157D, base 157B, ovary; 138A in color, covered with very small glands.

*Fruit and seed.*—Fruit and seeds have not been observed to date.

It is claimed:

1. A new and distinct cultivar of *Deutzia* plant named 'LISSTODEL' as herein illustrated and described.

* * * * *